US012714660B2

(12) United States Patent
Faig et al.

(10) Patent No.: US 12,714,660 B2
(45) **Date of Patent: *Aug. 25, 2026**

(54) COSMETIC COMPOSITIONS COMPRISING HIGH AMOUNTS OF HYDROXYPROPYL TETRAHYDROPYRANTRIOL

(71) Applicant: L'OREAL

(72) Inventors: Jonathan James Faig, Sayreville, NJ (US); Yon Jae Yoon, Roselle, NJ (US); Susan Halpern Chirch, Basking Ridge, NJ (US); Angelike Galdi, Westfield, NJ (US)

(73) Assignee: L'OREAL, Paris (FR)

( * ) Notice: Subject to any disclaimer, the term of this patent is extended or adjusted under 35 U.S.C. 154(b) by 882 days.

This patent is subject to a terminal disclaimer.

(21) Appl. No.: 18/050,706

(22) Filed: Oct. 28, 2022

(65) Prior Publication Data

US 2023/0139504 A1 May 4, 2023

Related U.S. Application Data

(60) Provisional application No. 63/273,963, filed on Oct. 31, 2021.

(30) Foreign Application Priority Data

Jan. 31, 2022 (FR) ...................................... 2200821

(51) Int. Cl.

| | |
|---|---|
| ***A61K 8/60*** | (2006.01) |
| ***A61K 8/06*** | (2006.01) |
| ***A61K 8/34*** | (2006.01) |
| ***A61K 8/37*** | (2006.01) |
| ***A61K 8/81*** | (2006.01) |
| ***A61K 8/92*** | (2006.01) |
| ***A61Q 19/00*** | (2006.01) |

(52) U.S. Cl.

CPC ................ *A61K 8/60* (2013.01); *A61K 8/062* (2013.01); *A61K 8/34* (2013.01); *A61K 8/342* (2013.01); *A61K 8/375* (2013.01); *A61K 8/8152* (2013.01); *A61K 8/922* (2013.01); *A61Q 19/00* (2013.01); *A61K 2800/10* (2013.01); *A61K 2800/48* (2013.01)

(58) Field of Classification Search

CPC ... A61K 8/31; A61K 8/37; A61K 8/39; A61K 8/60; A61K 8/602; A61K 8/4993; A61Q 19/08

USPC ........................................................... 514/23

See application file for complete search history.

(56) References Cited

U.S. PATENT DOCUMENTS

| | | | | |
|---|---|---|---|---|
| 8,617,578 | B2 | 12/2013 | Fares et al. | |
| 8,637,057 | B2 | 1/2014 | Patel et al. | |
| 8,758,215 | B2 | 6/2014 | Legendre et al. | |
| 9,017,391 | B2 | 4/2015 | McDaniel | |
| 9,144,690 | B2 | 9/2015 | McDaniel | |
| 9,227,082 | B2 | 1/2016 | McDaniel | |
| 10,426,723 | B2 * | 10/2019 | Gan | A61Q 19/00 |
| 10,449,133 | B1 * | 10/2019 | Faig | A61K 8/4973 |
| 10,898,496 | B2 | 1/2021 | Simard | |
| 10,940,103 | B2 | 3/2021 | Faig et al. | |
| 10,973,749 | B2 | 4/2021 | Sverdlove et al. | |
| 11,058,614 | B2 | 7/2021 | Choi et al. | |
| 12,064,504 | B2 * | 8/2024 | Faig | A61K 8/922 |
| 12,090,224 | B2 * | 9/2024 | Faig | A61Q 19/00 |
| 2002/0019547 | A1 | 2/2002 | Tuloup et al. | |
| 2002/0058010 | A1 | 5/2002 | Picard-Lesboueyries et al. | |
| 2002/0182238 | A1 | 12/2002 | Creton | |
| 2002/0197289 | A1 | 12/2002 | Chevalier et al. | |
| 2003/0215413 | A1 | 11/2003 | Fares et al. | |
| 2004/0137024 | A1 | 7/2004 | Abriat et al. | |
| 2004/0162272 | A1 | 8/2004 | Hansenne et al. | |
| 2005/0191337 | A1 | 9/2005 | Gueret | |
| 2006/0026775 | A1 | 2/2006 | Rozot et al. | |
| 2007/0015840 | A1 | 1/2007 | Dalko et al. | |
| 2007/0202065 | A1 | 8/2007 | Devin-Baudoin et al. | |
| 2007/0202203 | A1 | 8/2007 | Amar | |
| 2007/0248633 | A1 | 10/2007 | Baldo | |
| 2008/0050333 | A1 | 2/2008 | Lemoine et al. | |
| 2008/0131391 | A1 | 6/2008 | Ellington et al. | |
| 2008/0153839 | A1 | 6/2008 | Cotton et al. | |
| 2008/0159970 | A1 | 7/2008 | Willemin | |
| 2008/0207570 | A1 | 8/2008 | Segura-Orsoni | |
| 2008/0226756 | A1 | 9/2008 | Willemin et al. | |

(Continued)

FOREIGN PATENT DOCUMENTS

| | | | |
|---|---|---|---|
| DE | 102017201050 | A1 | 7/2018 |
| EP | 1493421 | B1 | 3/2007 |

(Continued)

OTHER PUBLICATIONS

Proksch, Journal of Dermatology, 2018, 45, 45, 1044-1052.*

(Continued)

*Primary Examiner* — Ganapathy Krishnan

(74) *Attorney, Agent, or Firm* — POLSINELLI PC

(57) ABSTRACT

The present disclosure relates to stable cosmetic compositions containing high amounts of hydroxypropyl tetrahydropyrantriol, and optionally containing 4-tert-cyclohexanol. The cosmetic compositions further include water, a plurality of emulsifiers, fatty alcohols, further fatty compounds, and thickening polymers. Methods for stabilizing the cosmetic compositions containing high amounts of hydroxypropyl tetrahydropyrantriol, and optionally 4-tert-cyclohexanol, and methods of treating the skin with the cosmetic compositions is also described.

18 Claims, No Drawings

(56) References Cited

U.S. PATENT DOCUMENTS

2008/0293962 A1 11/2008 Dalko et al.
2009/0016971 A1 1/2009 Gaudry et al.
2009/0016974 A1 1/2009 Pruche et al.
2009/0018200 A1 1/2009 Willemin et al.
2009/0041691 A1 2/2009 Candau et al.
2009/0285868 A1 11/2009 Richard et al.
2009/0317430 A1 12/2009 Cassin et al.
2010/0086502 A1 4/2010 Lucet-Levannier et al.
2010/0112100 A1 5/2010 Willemin et al.
2010/0189675 A1 7/2010 Pelletier
2010/0197805 A1 8/2010 Cassin
2011/0021438 A1 1/2011 Dalko et al.
2011/0130704 A1 6/2011 Baldo et al.
2013/0259912 A1 10/2013 Suzuki et al.
2013/0344015 A1 12/2013 Gaudry et al.
2014/0287005 A1 9/2014 Chevalier et al.
2015/0047664 A1 2/2015 Samain et al.
2015/0157539 A1 6/2015 Shimizu et al.
2015/0174047 A1 6/2015 Chiou et al.
2015/0174050 A1 6/2015 Lu et al.
2015/0265504 A1 9/2015 Crane et al.
2015/0265825 A1 9/2015 Miller et al.
2016/0213599 A1 7/2016 Devie
2016/0220308 A1 8/2016 Khormaei et al.
2016/0220804 A1 8/2016 Khormaei et al.
2017/0151538 A1 6/2017 Balooch et al.
2017/0154372 A1 6/2017 Balooch et al.
2017/0189277 A1 7/2017 Matsufuji et al.
2017/0326045 A1 11/2017 Lorant et al.
2017/0348221 A1 12/2017 Maruyama et al.
2018/0085721 A1 3/2018 Rinaldis et al.
2018/0243182 A1 8/2018 Ricard et al.
2018/0344609 A1 12/2018 Lu et al.
2019/0038539 A1 2/2019 Garruto et al.
2019/0110967 A1 4/2019 Chiou
2019/0159980 A1 5/2019 Chen et al.
2020/0211078 A1 7/2020 Balooch et al.
2020/0246228 A1 8/2020 Maczkiewitz et al.
2020/0253853 A1 8/2020 Lu et al.
2020/0277093 A1 9/2020 Besen et al.
2021/0015719 A1 1/2021 Lu et al.
2021/0093529 A1 4/2021 LaRosa et al.
2021/0093539 A1 * 4/2021 LaRosa .................. A61K 8/416
2021/0186829 A1 6/2021 Simonnet et al.

FOREIGN PATENT DOCUMENTS

EP 1961455 A1 8/2008
EP 3082974 A1 10/2016
FR 2973237 A1 10/2012
FR 2984742 A1 6/2013
FR 3059545 A1 6/2018
WO 2011030308 A1 3/2011
WO 2021180400 A1 9/2021

OTHER PUBLICATIONS

"Beiersdorf Personalizes Face Care with Launch of New Brand O.W.N." Newsroom-Press Releases, 2021, pp. 1-2.
Kacey Culliney, "Beiersdorf files patent on AI skin profiling and product recommendation method," 2021, pp. 1-3.
Preliminary Search Report and Written Opinion issued on Oct. 12, 2022 for corresponding French Application No. 2200821.
Database GNPD [Online] MINTEL;. Anonymous: "Personalised Anti-Aging Care [Integral Care] + [Marine Collagen Booster]"; 2021 XP055969412.
Database GNPD [Online] MINTEL; Anonymous: "The Night Cream & Mask"; 2017 XP055969427.
Database GNPD [Online] MINTEL; Anonymous: "Hand, Neck & Decollete Complexion Homogenizer Repairing Cream SPF 15"; 2019 XP055969424.
Database GNPD [Online] MINTEL; Anonymous: "Anti-Ageing BB Cream SPF 15"; 2020 XP055969430.

* cited by examiner

COSMETIC COMPOSITIONS COMPRISING HIGH AMOUNTS OF HYDROXYPROPYL TETRAHYDROPYRANTRIOL

CROSS-REFERENCE TO RELATED APPLICATIONS

This application claims benefit of U.S. Ser. No. 63/273,963 filed Oct. 31, 2021, and benefit of French Application No. FR 2200821, filed on Jan. 31, 2022, which are incorporated herein by reference in their entirety.

FIELD OF THE DISCLOSURE

The instant disclosure relates to stable cosmetic compositions that include high amounts of hydroxypropyl tetrahydropyrantriol; and to methods for stabilizing the cosmetic composition containing high amounts of hydroxypropyl tetrahydropyrantriol. The instant disclosure also describes methods for treating skin with the cosmetic compositions.

SUMMARY

In an aspect, the present disclosure is directed to, among other things, cosmetic compositions including a surprisingly high amount of hydroxypropyl tetrahydropyrantriol. In various embodiments, the compositions additionally include surprisingly high amounts of 4-tert-cyclohexanol. However, the inclusion of 4-tert-cyclohexanol is not required and in some embodiment is not included in the cosmetic compositions. These active ingredients provide a myriad of cosmetic benefits to the skin but have historically been very difficult to incorporate into stable cosmetic compositions, especially in high amounts. The inventors of the instant disclosure developed, among other things, surprisingly stable compositions that include high amounts of hydroxypropyl tetrahydropyrantriol, and optionally high amounts of 4-tert-cyclohexanol. Due to the high amounts of these ingredients, the cosmetic compositions provide exceptional cosmetic properties to the skin. Due to the high amounts of hydroxypropyl tetrahydropyrantriol, the cosmetic compositions reduce the appearance of fine lines and wrinkles, improve production of hyaluronic acid via stimulation of glycosaminoglycan (GAG) synthesis, thereby softening of stratum corneum to relieve cumulative stress on the epidermis and dermis, etc. Due to the high amounts of 4-tert-butylcyclohexanol, the cosmetic compositions reduce skin irritation, sooth the skin, and/or reduce or alleviate stinging, burning, and tightness.

In an aspect, the present disclosure is directed to, among other things, a cosmetic composition in the form of an oil in water emulsion, preferably a gel emulsion. In an embodiment, the cosmetic composition includes:

(a) hydroxypropyl tetrahydropyrantriol;
(b) water;
(c) one or more nonionic emulsifiers chosen from glyceryl esters having an HLB of about 3 to about 8;
(d) one or more nonionic emulsifiers having an HLB of about 16 to about 18;
(e) one or more nonionic emulsifiers having an HLB of about 9 to about 15;
(f) one or more fatty alcohols;
(g) one or more fatty compounds; and
(h) one or more thickening polymers.

wherein all percentages by weight are based on the total weight of the cosmetic composition.

Among nonionic emulsifiers, nonlimiting examples of glyceryl esters having an HLB of about 3 to about 8 include glyceryl behenate, glyceryl erucate, glyceryl hydroxystearate, glyceryl isostearate, glyceryl lanolate, glyceryl laurate, glyceryl linoleate, glyceryl myristate, glyceryl palmitate lactate, glyceryl stearate, glyceryl distearate, glyceryl laurate, or a mixture thereof. In at least one instance the glyceryl ester comprises glyceryl stearate, glyceryl ricinoleate, and mixtures thereof Nonlimiting examples of nonionic emulsifiers having an HLB of about 16 to about 18 include ethoxylated emulsifiers, for example, ethoxylated fatty acids, ethoxylated sorbitan fatty esters, and mixtures thereof. Ethoxylated fatty acids are particularly preferred.

Nonlimiting examples of nonionic emulsifiers having an HLB of about 9 to about 15 include alkylpolyglucosides (cetearyl glucoside), polyglycerol-based emulsifiers (polyglyceryl-3 methylglucose distearate), sorbitan fatty esters (polysorbate 60), sugar esters or ethers, sugar-based esters or ethers, polyol fatty esters or ethers, glyceryl fatty esters or ethers, ethoxylates thereof, or mixtures thereof.

Nonlimiting examples of fatty alcohols include fatty alcohols having from 8 to 24 carbon atoms, in particular, cetyl alcohol, stearyl alcohol, cetearyl alcohol, behenyl alcohol, lauryl alcohol, myristic or myristyl alcohol, arachidyl alcohol, and mixtures thereof.

Nonlimiting examples of fatty compounds include fatty esters (e.g., isononyl isononanoate), polyolefins (petrolatum), waxes, squalane, squalene, hydrogenated polyisobutene, hydrogenated polydecene, polybutene, mineral oil, pentahydrosqualene, plant and/or vegetable oil (e.g., soybean oil), hydrocarbon-based oils (e.g., isohexadecane), and a mixture thereof.

Useful thickening polymers include, among others, taurate copolymers. Nonlimiting examples include acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and mixtures thereof.

Silicones can optionally be included in the cosmetic compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes. In some instances, the cosmetic compositions of the instant case are free or essentially free from silicones, such as dimethicones, amodimethicones, dimethiconols, cyclosiloxanes, siloxanes, etc.

In an embodiment, the cosmetic compositions form part of a kit comprising a cosmetic composition according to the instant disclosure and one or more separately contained compositions. In an embodiment, the compositions are received in a device, for example, a device that dispenses the cosmetic composition and the one or more separately contained compositions. In an embodiment, the device dispenses the cosmetic composition and the one or more separately contained compositions without mixing them together prior to dispensing. Even though high amounts of hydroxypropyl tetrahydropyrantriol are incorporated into the cosmetic compositions, and optionally, high amounts of tert-butylcyclohexanol, the compositions are unique in that they are compatible with other cosmetic compositions, in particular, other cosmetic compositions for treating the skin.

Another aspect of the instant disclosure relates to methods for stabilizing high amounts of hydroxypropyl tetrahydropyrantriol into cosmetic compositions; and to methods for stabilizing high amounts of tert-butylcyclohexanol into the cosmetic compositions. These methods, as describe throughout the disclosure, comprise incorporating the high amounts of hydroxypropyl tetrahydropyrantriol, and optionally, high amounts of tert-butylcyclohexanol, into the compositions of the instant disclosure.

Another aspect of the instant disclosure relates to methods for treating skin. The methods include applying the cosmetic composition according to the instant disclosure to the skin. In an embodiment, the methods reduce the appearance of fine lines and wrinkles, improve production of hyaluronic acid via stimulation of glycosaminoglycan (GAG) synthesis, thereby softening of stratum corneum to relieve cumulative stress on the epidermis and dermis, etc. When tert-butylcyclohexanol is included in the compositions, the methods further treat skin irritation, sooth the skin, and/or reduce or alleviate stinging, burning, and tightness.

Other features and iterations of the invention are described in more detail below.

DETAILED DESCRIPTION

A common problem associated with formulating compositions, especially composition comprising multiple components, is ensuring physical stability, chemical stability, solubility, and the like. Many additives for food, cosmetics, personal care, and household products into which they are incorporated are difficult to stabilize and solubilize, especially when used in high amounts. The consequence of stability and solubility problems is significant. For example, stability problems can cause partial, if not complete, loss of product integrity, color loss, malodor, viscosity changes, etc. Stability problems can also cause an increased or a decreased amount of the component in question to be applied. With respect to active ingredients, stability problems reduce or eliminate activity, and prevent the active ingredients from reaching their intended target in the desired amount.

With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. This is known as elastosis. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively influence the skin, causing dryness, rash, and puffiness.

Human skin acts as a primary barrier between the body and its environment. Crucial for this skin barrier function is the lipid matrix in the outermost layer of the skin (epidermis), the stratum corneum (SC). Two of its functions are (1) to prevent excessive water loss through the epidermis and (2) to avoid that compounds from the environment permeate into the viable epidermal and dermal layers and thereby provoke an immune response. The composition of the SC lipid matrix is dominated by three lipid classes: cholesterol, free fatty acids, and ceramides. These lipids adopt a highly ordered, 3-dimensional structure of stacked densely packed lipid layers (lipid lamellae): the lateral and lamellar lipid organization. The way in which these lipids are ordered depends on the composition of the lipids. One very common skin disease in which the SC lipid barrier is affected is atopic dermatitis (AD).

What is needed, among other things, are compositions which include high amounts of hydroxypropyl tetrahydropyrantriol; and compositions that further include high amounts of 4-tert-cyclohexanol.

In an aspect, the present disclosure is directed to, among other things, a stable cosmetic composition that includes high amounts of hydroxypropyl tetrahydropyrantriol, and optionally include high amounts of 4-tert-butylcyclohexanol; and to methods for stabilizing cosmetic compositions containing high amounts of hydroxypropyl tetrahydropyrantriol, and optionally high amounts of 4-tert-butylcyclohexanol. In an embodiment, the compositions include:

(a) about 10 to about 40 wt. % of hydroxypropyl tetrahydropyrantriol;
(b) water;
(c) about 0.1 to about 5 wt. % of nonionic emulsifier chosen from glyceryl esters having an HLB of about 3 to about 8;
(d) about 0.1 to about 5 wt. % of one or more nonionic emulsifiers having an HLB of about 16 to about 18;
(e) about 0.1 to about 5 wt. % of one or more nonionic emulsifiers having an HLB of about 9 to about 15;
(f) about 1 to about 10 wt. % of one or more fatty alcohols;
(g) about 5 to about 20 wt. % of one or more fatty compounds; and
(h) one or more thickening polymers;
 wherein the composition is in the form of an oil in water emulsion, preferably a gel emulsion, and all percentages by weight are based on the total weight of the cosmetic composition.

A gel emulsion is an oil in water emulsion, wherein the aqueous phase is a gel and the oil droplets/particulates are dispersed throughout the gel matrix.

(a) Hydroxypropyl Tetrahydropyrantriol

Hydroxypropyl tetrapyrantriol is a sugar-protein hybrid made from xylose and can effectively activate the synthesis of GAGs (glycosamineoglycans), promote the production of hyaluronic acid, synthesis of collagen, adhesion between the dermis and the epidermis, the synthesis of epidermal structural components, the regeneration of damaged tissue, and maintain skin elasticity.

The amount of hydroxypropyl tetrapyrantriol in the cosmetic compositions will vary but in various embodiment it is from about 10 wt. % to about 40 wt. % based on the total weight of the composition. In further embodiments, the amount of hydroxypropyl tetrapyrantriol in the composition is from about 10 wt. % to about 35 wt. %, from about 10 to about 30 wt. %, from about 10 to about 25 wt. %, from about 10 to about 20 wt. %, about 12 to about 35 wt. %, about 12 to about 30 wt. %, about 12 to about 25 wt. %, about 12 to about 20 wt. %, from about 12 to about 18 wt. %, from about 14 to about 30 wt. %, from about 14 to about 25 wt. %, from about 14 to about 20 wt. %, or from about 14 to about 18 wt. %, based on the total weight of the composition.

(b) Water

The amount of water in the cosmetic compositions can and will vary depending on the amount of the other components in the cosmetic compositions. In general, the amount of water in the composition is from about 30 to about 85 wt. %, based on the total weight of the cosmetic composition. In various embodiments, the amount of water in the cosmetic composition is from about 30 to about 80 wt.

%, about 30 to about 70 wt. %, about 30 to about 60 wt. %, about 30 to about 50 wt. %, about 40 to about 80 wt. %, about 40 to about 70 wt. %, about 40 to about 60 wt. %, about 40 to about 50 wt. %, about 50 to about 80 wt. %, about 50 to about 75 wt. %, about 50 to about 70 wt. %, about 55 to about 85 wt. %, about 55 to about 80 wt. %, about 55 to about 75 wt. %, about 55 to about 70 wt. %, about 60 to about 85 wt. %, about 60 to about 80 wt. %, about 60 to about 75 wt. %, or about 60 to about 70 wt. %, based on the total weight of the cosmetic composition.

(c) Nonionic Emulsifiers/Glyceryl Esters

The cosmetic composition of the instant disclosure includes one or more nonionic emulsifiers chosen from glyceryl esters having an HLB of about 3 to about 8. Nonlimiting examples include glyceryl behenate, glyceryl erucate, glyceryl hydroxystearate, glyceryl lanolate, glyceryl laurate, glyceryl linoleate, glyceryl myristate, glyceryl palmitate lactate, glyceryl stearate, glyceryl distearate, or a mixture thereof. preferred glyceryl esters include glyceryl stearate, glyceryl ricinoleate, or a mixture thereof.

In various embodiments, the one or more glyceryl esters having an HLB of about 3 to about 8 are chosen from glyceryl esters that are solid at a temperature of below 30° C.

The total amount of the one or more nonionic emulsifiers chosen from one or more glyceryl esters having an HLB of about 3 to about 8 can vary. In an embodiment, the amount of the nonionic emulsifier chosen from one or more glyceryl esters having an HLB of about 3 to about 8 is from 0.1 wt. % to about 5 wt. % based on the total weight of the cosmetic composition. In further embodiments, the amount of the nonionic emulsifier chosen from one or more glyceryl esters having an HLB of about 3 to about 8 is from about 0.1 to about 4 wt. %, from about 0.1 to about 3 wt %, from about 0.1 to about 2 wt %, about 0.2 wt. % to about 5 wt. %, about 0.2 to about 4 wt. %, from about 0.2 to about 3 wt %, from about 0.2 to about 2 wt %, about 0.3 wt. % to about 5 wt. %, about 0.3 to about 4 wt. %, from about 0.3 to about 3 wt %, from about 0.3 to about 2 wt %, about 0.5 wt. % to about 5 wt. %, about 0.5 to about 4 wt. %, from about 0.5 to about 3 wt %, from about 0.5 to about 2 wt %, based on the total weight of the cosmetic composition.

(d) Nonionic Emulsifiers Having an HLB of about 16 to about 18

Nonlimiting examples of nonionic emulsifiers having an HLB of about 16 to about 18 include ethoxylated emulsifiers, for example, ethoxylated fatty acids, ethoxylated sorbitan fatty esters, and mixtures thereof. In some instances, it is preferably that the nonionic emulsifiers having an HLB of about 16 to about 18 include one or more ethoxylated fatty acids.

Nonlimiting examples of ethoxylated fatty acids include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

Nonlimiting examples of ethoxylated sorbitan fatty esters include polysorbate-20 (POE(20) sorbitan monolaurate), polysorbate-21 (POE(4) sorbitan monolaurate), polysorbate-40 (POE(20) sorbitan monopalmitate), polysorbate-60 (POE (20) sorbitan monostearate), polysorbate-61 (POE(4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate and sorbitan tristearate and a mixture thereof.

The total amount of the one or more nonionic emulsifiers having an HLB of about 16 to about 18 will vary. Nonetheless, in an embodiment, the amount of the one or more nonionic emulsifiers having an HLB of about 16 to about 18 is from about 0.1 to about 5 wt. %, based on the total weight of the cosmetic composition. In further embodiments, the amount of the one or more nonionic emulsifiers having an HLB of about 16 to about 18 range from about 0.1 to about 4 wt %, from about 0.1 to about 3 wt %, from about 0.1 to about 2 wt %, about 0.2 wt. % to about 5 wt. %, about 0.2 to about 4 wt. %, from about 0.2 to about 3 wt %, from about 0.2 to about 2 wt %, about 0.3 wt. % to about 5 wt. %, about 0.3 to about 4 wt. %, from about 0.3 to about 3 wt %, from about 0.3 to about 2 wt %, about 0.5 wt. % to about 5 wt. %, about 0.5 to about 4 wt. %, from about 0.5 to about 3 wt %, from about 0.5 to about 2 wt %, based on the total weight of the cosmetic composition.

(e) Nonionic Emulsifiers Having an HLB of about 9 to about 15

Nonlimiting examples of nonionic emulsifiers having an HLB of about 9 to about 15 include alkylpolyglucosides (cetearyl glucoside), polyglycerol-based emulsifiers (polygyceryl-3 methylglucose distearate), sorbitan fatty esters (polysorbate 60), sugar esters or ethers, sugar-based esters or ethers, polyol fatty esters or ethers, glyceryl fatty esters or ethers, ethoxylates thereof, or mixtures thereof In a preferred embodiment, one or more of the nonionic emulsifiers having an HLB of about 9 to about 15 are sugar esters or ethers or sugar-based esters and ethers. “Sugar ester” as used herein means “sugar alcohol fatty acid ester” or “sugar acid fatty alcohol ester” and “sugar ether” as used herein means “sugar alcohol fatty alcohol ether.” The sugar-based esters and ethers of can be esters or ethers of (a) a sugar, a sugar alcohol, or a sugar derivative and (b) a fatty acid or fatty alcohol. In some embodiments, esters may be preferred over ethers, and vice-versa. The esters and ethers may be formed by the combination of a sugar, sugar alcohol, or sugar derivative with a fatty acid, or by the combination of a sugar, sugar alcohol, or sugar derivative with a fatty alcohol. For example, a sucrose laurate ester may be formed by the combination of sucrose with lauric acid or lauryl sucronic acid ester, and unless otherwise specified herein, it is not necessary to the present embodiments that a particular ester (or ether) is the result of esterification (or etherification) with a fatty acid as opposed to a fatty alcohol, or vice-versa.

Preferred sugars of the esters and ethers include monosaccharides, disaccharides, and oligosaccharides, and in a preferred embodiment, the sugar is a mono-, di-, or trisaccharide, or a mixture thereof. Exemplary sugars include allose, altrose, arabinose, cellobiose, erythrose, erythrulose, fructose, fucose, galactose, gentiobiose, glucose, gulose, idose, isomaltose, lactose, lactulose, lyxose, maltose, maltotriose, mannobiose, mannose, melezitose, raffinose, rhamnose, ribose, ribulose, sorbose, sucrose, talose, threose, trehalose, xylobiose, xylose and xylulose. In a preferred embodiment, the sugar is glucose or sucrose. Exemplary sugar alcohols include allitol, arabitol, ducitol, erythritol, galactitol, glycerol, glycol, iditol, inositol, isomalt, lactitol, mallitol, maltitol, mannitol, sorbitol, and xylitol. Exemplary sugar derivatives such as sulfonated sugars and sugar amines can also be used in the present embodiments. These examples are non-limiting examples, and it should be understood that any saccharide, sugar alcohol, or other sugar derivative that will provide a hydrophilic head group to the ester or ether and is otherwise pharmaceutically acceptable is suitable for use in the present embodiments.

The fatty acids and fatty alcohols used in the esters and ethers may be any fatty acid or fatty acid alcohol capable of providing a hydrophobic tail group such that the ester or ether can exert surface active properties. The fatty acids and fatty alcohols can be short chain (i.e., less than 8 carbons in length), medium chain (i.e., 8 to 14 carbons in length), or long chain (i.e., more than 14 carbons in length). Branched or unbranched fatty acids and fatty alcohols can be used. Non-limiting examples of suitable saturated fatty acids include butyric, caproic, caprylic, capric, lauric, myristic, palmitic, stearic, arachidic, and behenic acids, and non-limiting examples of suitable unsaturated fatty acids include myristoleic, palmitoleic, oleic, linoleic, linolenic, arachidonic, eicosapentaenoic, erucic, and docosahexaenoic acids. Non-limiting examples of suitable linear fatty alcohols include caproyl(caproic), caprylic, capric, lauryl, myristyl, palmityl(cetyl), palmitoleyl, stearyl, oleyl, linoleyl, linolenyl, arachidyl, behenyl, erucyl and lignoceryl alcohols, and non-limiting examples of suitable branched fatty alcohols include isocetyl, isostearyl, and isobehenyl alcohols.

In a preferred embodiment, the fatty component of the sugar-based ester or ether is a $C_{12}$ fatty component (e.g., stearic acid, stearyl alcohol, lauric acid, lauryl alcohol, etc.), or a $C_8$ to $C_{18}$ fatty component. In another embodiment, a mixture of medium and long chain fatty components is preferred, particularly a mixture of saturated and unsaturated $C_8$ to $C_{18}$ fatty components. In yet another embodiment, a mixture of saturated and unsaturated $C_8$ to $C_{18}$ fatty acids is preferred. In a different embodiment, the sugar-based ester or ether is a di- or tri-ester of a fatty acid or alcohol, or a di- or tri-ether of a fatty alcohol.

The sugar-based esters and ethers can be monoesters or monoethers, or can be di-, tri-, or poly-esters and ethers, depending on the sugar or sugar alcohol selected for use. In an embodiment, mono- and di-esters, or mono- and di-ethers are preferred. The esterification and etherification may occur at any free hydroxyl group in the sugar or sugar alcohol.

Mixtures of esters or ethers are also contemplated for use. The mixtures may be varied in a number of ways. For example, a particular ester used in a formulation, such as a sugar monostearate, may comprise a variety of sugar monostearate esters, each esterified at a different hydroxyl group. Or, for example, a sugar stearate may comprise a variety of esters with varying degrees of esterification, for example a monostearate, a distearate, a tristearate, etc. Or, in yet another example, a sugar mono acid or sugar diacid may comprise mono- or di-esterification with stearyl alcohol fatty component. In still another example, a mixture containing a particular ester such as a sugar stearate may contain predominantly esters of stearyl acid (or stearyl alcohol), but also contain esters of other fatty components, such as, e.g., esters of myristic acid (or myristyl alcohol), etc. In yet another example, an "ester" may already be a mixture of fatty acids to form the esters, for example the "ester" sucrose cocoate is actually a mixture of esters including the laurate, palmitic, myristic, stearic and caproic esters of sucrose with smaller quantities of other short and long chain fatty acids as well as mixed di- and tri-esters. These non-limiting examples of mixtures apply equally to sugar-based ethers as well as esters.

The sugar-based esters and ethers may be prepared by any suitable means known in the art, for example by incubating an aqueous mixture of a sugar or sugar-alcohol, a fatty acid and a catalytically active amount of a lipolytic enzyme, and recovering the resulting ester from the mixture. Other methods include admixing the sugar with a fatty acid chloride at about 80° C., with simple removal of the hydrogen chloride formed and recovery of the sugar fatty acid ester. Similarly, a mixture of a methyl fatty acid ester and sugar can be heated at a temperature of about 90° C. in the presence of a base catalyst, distilling the methanol formed and recovering the sugar fatty acid ester. Many suitable esters and ethers are also commercially available.

The fatty acid esters of sugars may be chosen in particular from the group comprising esters or mixtures of esters of $C_8$-$C_{22}$ fatty acid and of sucrose, of maltose, of glucose or of fructose, and esters or mixtures of esters of $C_{14}$-$C_{22}$ fatty acid and of methylglucose.

The $C_8$-$C_{22}$ or $C_{14}$-$C_{22}$ fatty acids forming the fatty unit of the esters which can be used comprise a saturated or unsaturated linear alkyl or alkenyl chain containing, respectively, from 8 to 22 or from 14 to 22 carbon atoms. The fatty unit of the esters may be chosen in particular from stearates, behenates, arachidonates, palmitates, myristates, laurates and caprates, and mixtures thereof. Stearates are preferably used.

As examples of esters or mixtures of esters of fatty acid and of sucrose, of maltose, of glucose or of fructose, mention may be made of sucrose monostearate, sucrose distearate and sucrose tristearate and mixtures thereof; and examples of esters or mixtures of esters of fatty acid and of methylglucose which may be mentioned are polyglyceryl-3 methylglucose distearate. Mention may also be made of glucose or maltose monoesters such as methyl o-hexadecanoyl-6-D-glucoside and o-hexadecanoyl-6-D-maltoside.

In an embodiment, the cosmetic composition preferably includes at least one ester of $C_{14}$-$C_{22}$ fatty acids and of methylglucose, for example, polyglyceryl-3 methylglucose distearate.

The fatty alcohol ethers of sugars, which can be used may be solid at a temperature of less than or equal to 45° C. and may be chosen in particular from the group comprising ethers or mixtures of ethers of $C_8$-$C_{22}$ fatty alcohol and of glucose, of maltose, of sucrose or of fructose, and ethers or mixtures of ethers of a $C_{14}$-$C_{22}$ fatty alcohol and of methylglucose. These are in particular, alkylpolyglucosides, which in various embodiments are preferred. A particularly preferred examples is C12-20 alkyl glucoside. Accordingly, in an embodiment, the cosmetic compositions include at least one alkylpolyglucosides, for example, C12-20 alkyl glucoside.

The $C_8$-$C_{22}$ or $C_{14}$-$C_{22}$ fatty alcohols forming the fatty unit of the ethers which may be used comprise a saturated or unsaturated, linear alkyl or alkenyl chain containing, respectively, from 8 to 22 or from 14 to 22 carbon atoms. The fatty unit of the ethers may be chosen in particular from decyl, cetyl, behenyl, arachidyl, stearyl, palmityl, myristyl, lauryl, capryl and hexadecanoyl units, and mixtures thereof, such as cetearyl.

As examples of fatty alcohol ethers of sugars, mention may be made of alkylpolyglucosides such as decylglucoside and laurylglucoside, cetostearyl glucoside, arachidyl glucoside, and mixtures thereof. Further mention is made of sucrose monostearate, sucrose distearate or sucrose tristearate and mixtures thereof, polyglyceryl-3 methylglucose distearate and alkylpolyglucosides.

In certain embodiments, the nonionic emulsifiers having an HLB from about 9 to about 15 may be chosen from: polyglyceryl fatty acid esters of at least one fatty acid comprising at least one saturated or unsaturated, linear or branched $C_8$-$C_{22}$ hydrocarbon group such as $C_8$-$C_{22}$ alkyl or alkenyl group, preferably $C_8$-$C_{18}$ alkyl or alkenyl group, and more preferably $C_8$-$C_{12}$ alkyl or alkenyl group, and of 2 to 12 glycerols, preferably 2 to 10 glycerols and more preferably 2 to 8 glycerols; polyoxyethylenated alkyl glycerides such as polyethylene glycol derivatives of a mixture of mono-, di- and tri-glycerides of caprylic and capric acids (preferably 2 to 30 ethylene oxide units, more preferably 2 to 20 ethylene oxide units, and even more preferably 2 to 10 ethylene oxide units); polyoxyethylenated fatty ethers of at least one, preferably one, fatty alcohol comprising at least one saturated or unsaturated, linear or branched $C_8$-$C_{22}$ hydrocarbon group such as $C_8$-$C_{22}$ alkyl or alkenyl group, preferably $C_8$-$C_{18}$ alkyl or alkenyl group, and more preferably $C_8$-$C_{12}$ alkyl or alkenyl group, and of 2 to 60 ethylene oxides, preferably from 2 to 30 ethylene oxides, and more preferably from 2 to 10 ethylene oxides; and mixtures thereof.

It is preferable that the polyglyceryl fatty acid ester have a polyglycerol moiety derived from 2 to 10 glycerols, more preferably from 2 to 8 glycerols, and further more preferably 4 to 6 glycerols. The polyglyceryl fatty acid ester may be chosen from the mono, di and tri esters of saturated or unsaturated acid, preferably saturated acid, including 8 to 22 carbon atoms, preferably 8 to 18 carbon atoms, and more preferably 8 to 12 carbon atoms, such as caprylic acid, capric acid, lauric acid, oleic acid, stearic acid, isostearic acid, and myristic acid.

The polyglyceryl fatty acid ester may be selected from the group consisting of PG2 caprate, PG2 dicaprate, PG2 tricaprate, PG2 caprylate, PG2 dicaprylate, PG2 tricaprylate, PG2 laurate, PG2 dilaurate, PG2 trilaurate, PG2 myristate, PG2 dimyristate, PG2 trimyristate, PG2 stearate, PG2 distearate, PG2 tristearate, PG2 isostearate, PG2 diisostearate, PG2 triisostearate, PG2 oleate, PG2 dioleate, PG2 trioleare, PG3 caprate, PG3 dicaprate, PG3 tricaprate, PG3 caprylate, PG3 dicaprylate, PG3 tricaprylate, PG3 laurate, PG3 dilaurate, PG3 trilaurate, PG3 myristate, PG3 dimyristate, PG3 trimyristate, PG3 stearate, PG3 distearate, PG3 tristearate, PG3 isostearate, PG3 diisostearate, PG3 triisostearate, PG3 oleate, PG3 dioleate, PG3 trioleare, PG4 caprate, PG4 dicaprate, PG4 tricaprate, PG4 caprylate, PG4 dicaprylate, PG4 tricaprylate, PG4 laurate, PG4 dilaurate, PG4 trilaurate, PG4 myristate, PG4 dimyristate, PG4 trimyristate, PG4 stearate, PG4 distearate, PG4 tristearate, PG4 isostearate, PG4 diisostearate, PG4 triisostearate, PG4 oleate, PG4 dioleate, PG4 trioleare, PG5 caprate, PG5 dicaprate, PG5 tricaprate, PG5 caprylate, PG5 dicaprylate, PG5 tricaprylate, PG5 laurate, PG5 dilaurate, PG5 trilaurate, PG5 myristate, PG5 dimyristate, PG5 trimyristate, PG5 stearate, PG5 distearate, PG5 tristearate, PG5 isostearate, PG5 diisostearate, PG5 triisostearate, PG5 oleate, PG5 dioleate, PG5 trioleare, PG6 caprate, PG6 dicaprate, PG6 tricaprate, PG6 caprylate, PG6 dicaprylate, PG6 tricaprylate, PG6 laurate, PG6 dilaurate, PG6 trilaurate, PG6 myristate, PG6 dimyristate, PG6 trimyristate, PG6 stearate, PG6 distearate, PG6 tristearate, PG6 isostearate, PG6 diisostearate, PG6 triisostearate, PG6 oleate, PG6 dioleate, PG6 trioleare, PG10 caprate, PG10 dicaprate, PG10 tricaprate, PG10 caprylate, PG10 dicaprylate, PG10 tricaprylate, PG10 laurate, PG10 dilaurate, PG10 trilaurate, PG10 myristate, PG10 dimyristate, PG10 trimyristate, PG10 stearate, PG10 distearate, PG10 tristearate, PG10 isostearate, PG10 diisostearate, PG10 triisostearate, PG10 oleate, PG10 dioleate, PG10 trioleare, and mixtures thereof.

The polyoxyalkylenated fatty ethers, preferably polyoxyethylenated fatty ethers, may comprise from 2 to 60 ethylene oxide units, preferably from 2 to 30 ethylene oxide units, and more preferably from 2 to 10 ethylene oxide units. The fatty chain of the ethers may be chosen in particular from lauryl, behenyl, arachidyl, stearyl and cetyl units, and mixtures thereof, such as cetearyl. Examples of ethoxylated fatty ethers which may be mentioned are lauryl alcohol ethers comprising 2, 3, 4, and 5 ethylene oxide units (CTFA names: Laureth-2, Laureth-3, Laureth-4, and Laureth-5).

The mixed esters of fatty acids, or of fatty alcohol, of carboxylic acid and of glycerol, which can be used as the above nonionic surfactant, may be chosen in particular from the group comprising mixed esters of fatty acid or of fatty alcohol with an alkyl or alkenyl chain containing from 8 to 22 carbon atoms, preferably from 8 to 18 carbon atoms, and more preferably from 8 to 12 carbon atoms, and of alpha-hydroxy acid and/or of succinic acid, with glycerol. The alpha-hydroxy acid may be, for example, citric acid, lactic acid, glycolic acid or malic acid, and mixtures thereof.

The alkyl chain of the fatty acids or alcohols from which are derived the mixed esters which can be used may be linear or branched, and saturated or unsaturated. They may especially be stearate, isostearate, linoleate, oleate, behenate, arachidonate, palmitate, myristate, laurate, caprate, isostearyl, stearyl, linoleyl, oleyl, behenyl, myristyl, lauryl or capryl chains, and mixtures thereof. nonlimiting examples of mixed esters include the mixed ester of glycerol and of the mixture of citric acid, lactic acid, linoleic acid and oleic acid (CTFA name: Glyceryl citrate/lactate/linoleate/oleate); the mixed ester of succinic acid and of isostearyl alcohol with glycerol (CTFA name: Isostearyl diglyceryl succinate); the mixed ester of citric acid and of stearic acid with glycerol (CTFA name: Glyceryl stearate citrate); the mixed ester of lactic acid and of stearic acid with glycerol (CTFA name: Glyceryl stearate lactate), and mixtures thereof.

The fatty esters of sorbitan and oxyalkylenated fatty esters of sorbitan may be chosen from the group comprising $C_{16}$-$C_{22}$ fatty acid esters of sorbitan and oxyethylenated $C_{16}$-$C_{22}$ fatty acid esters of sorbitan. They may be formed from at least one fatty acid comprising at least one saturated linear alkyl chain containing, respectively, from 16 to 22 carbon atoms, and from sorbitol or from ethoxylated sorbitol. The oxyethylenated esters may generally comprise from 1 to 100 ethylene glycol units and preferably from 2 to 40 ethylene oxide (EO) units. These esters may be chosen in particular from stearates, behenates, arachidates, palmitates, and mixtures thereof. Stearates and palmitates are preferably used. Nonlimiting examples include sorbitan monostearate (CTFA name: sorbitan stearate), sorbitan monopalmitate (CTFA name: sorbitan palmitate), sorbitan tristearate 20 EO (CTFA name: polysorbate 65), and mixtures thereof.

The block copolymers of ethylene oxide (A) and of propylene oxide (B), which may be used may be chosen in particular from block copolymers of formula

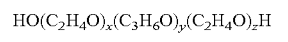

$$HO(C_2H_4O)_x(C_3H_6O)_y(C_2H_4O)_zH$$

in which x, y and z are integers such that x+z ranges from 2 to 100 and y ranges from 14 to 60, and mixtures thereof.

The polyoxyethylenated (1-40 EO) and polyoxypropylenated (1-30 PO) alkyl ($C_{16}$-$C_{30}$) ethers, which may be used as the above nonionic surfactant, may be selected from PPG-6 Decyltetradeceth-30; Polyoxyethlene (30) Polyoxypropylene (6) Tetradecyl Ether; PPG-6 Decyltetradeceth-12; Polyoxyethylene (12) Polyoxypropylene (6) Tetradecyl Ether; PPG-13 Decyltetradeceth-24; Polyoxyethylene (24) Polyoxypropylene (13) Decyltetradecyl Ether, PPG-6 Decyltetradeceth-20; Polyoxyethylene (20) Polyoxypropylene (6) Decyltetradecyl Ether, PPG-4 Ceteth-1; Polyoxyethylene (1) Polyoxypropylene (4) Cetyl Ether, PPG-8 Ceteth-1; Polyoxyethylene (1) Polyoxypropylene (8) Cetyl Ether, PPG-4 Ceteth-10; Polyoxyethylene (10) Polyoxypropylene (4) Cetyl Ether, PPG-4 Ceteth-20; Polyoxyethylene (20) Polyoxypropylene (4) Cetyl Ether, PPG-5 Ceteth-20; Polyoxyethylene (20) Polyoxypropylene (5) Cetyl Ether, PPG-8 Ceteth-20; Polyoxyethylene (20) Polyoxypropylene (8) Cetyl Ether, and PPG-23 Steareth-34; Polyoxyethylene Polyoxypropylene Stearyl Ether (34 EO) (23 PO).

In various embodiments, it may be more preferable that the polyoxyethylenated (1-40 EO) and polyoxypropylenated (1-30 PO) alkyl ($C_{16}$-$C_{30}$) ethers are (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-6 Decyltetradeceth-20, PPG-5 Ceteth-20, PPG-8 Ceteth-20, and PPG-23 Steareth-34. It may be even more preferable that the polyoxyethylenated (1-40 EO) and polyoxypropylenated (1-30 PO) alkyl ($C_{16}$-$C_{30}$) ethers are (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-5 Ceteth-20, and PPG-8 Ceteth-20.

In an embodiment, the one or more nonionic emulsifiers having an HLB from 9 to 12 may be chosen from alkylpolyglucosides (e.g., C12-20 alkyl glucoside), polyglyceryl-10 laurate, polyglyceryl-2 dipolyhydroxystearate, polyglyceryl-2 polyhydroxystearate, polyglyceryl-3 caprylate, polyglyceryl-3 laurate, polyglyceryl-3 methylglucose distearate, polyglyceryl-3 oleate, polyglyceryl-3 palmitate, polyglyceryl-3 polyricinoleate, polyglyceryl-3 ricinoleate, polyglyceryl-5 laurate, polyglyceryl-6 dicaprate, polyglyceryl-6 oleate, polyglyceryl-6 stearate, and a mixture thereof.

The total amount of the one or more nonionic emulsifiers having an HLB of about 9 to about 15 will vary. Nonetheless, in various embodiments, the amount of the one or more nonionic emulsifiers having an HLB of about 9 to about 15 is from about 0.1 to about 5 wt. %, based on the total weight of the cosmetic composition. In further embodiments, the one or more nonionic emulsifiers having an HLB of about 9 to about 15 is from about 0.1 to about 4 wt %, from about 0.1 to about 3 wt %, from about 0.1 to about 2 wt %, about 0.3 to about 5 wt. %, about 0.3 to about 4 wt. %, about 0.3 to about 2 wt. %, about 0.5 to about 5 wt. %, about 0.5 to about 4 wt. %, about 0.5 to about 3 wt. %, or about 0.5 to about 2 wt. %, about 1.0 to about 5 wt. %, about 1.0 to about 4 wt. %, about 1.0 to about 3 wt. %, or about 1.0 to about 2 wt. %, based on the total weight of the cosmetic composition.

(f) Fatty Alcohols

The term "fatty alcohol" means an alcohol comprising at least one hydroxyl group (OH), and comprising at least 8 carbon atoms, preferably at least 12 carbon atoms and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In certain embodiments, it is preferable that the cosmetic compositions include at least one solid fatty alcohol, in particular saturated fatty alcohols that are solid at 25° C., preferably having at least 12 carbon atoms.

The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

In an embodiment, the solid fatty alcohols are represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

Non-limiting examples of useful fatty alcohols include lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol), and mixtures thereof.

In certain embodiments, the one or more fatty alcohols have from 12 to 24 carbon atoms. Specific nonlimiting examples include cetyl alcohol, stearyl alcohol, cetearyl alcohol, behenyl alcohol, lauryl alcohol, myristic or myristyl alcohol, arachidyl alcohol, lignoceryl alcohol, or mixtures thereof.

Preferably, the cosmetic composition includes one or more solid fatty alcohols, for example, chosen from cetyl alcohol, stearyl alcohol, behenyl alcohol and mixtures thereof, preferably cetyl alcohol, behenyl alcohol, cetearyl alcohol, and mixtures thereof.

In some instances, the cosmetic compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the cosmetic compositions preferably include cetyl alcohol, behenyl alcohol, and cetearyl alcohol.

The total amount of the one or more fatty alcohols will vary. Nonetheless, in various embodiments, the total amount of the one or more fatty alcohols in the cosmetic compositions is from 1 wt. % to about 10 wt. %, based on the total weight of the composition. In further embodiments, the total amount of one or more fatty alcohols in the composition ranges from about 1 to about 8 wt. %, about 1 to about 5 wt. %, about 1 to about 4 wt. %, about 1 to about 3 wt. %, based on the total weight of the composition.

(g) Fatty Compounds

The term "fatty compounds" is interchangeable with the "fatty materials." Fatty compounds are known as compounds that are not soluble (or only sparingly soluble) in water; they are hydrophilic and are often solubilized in organic solvents. They include materials such as oils, fats, waxes, hydrocarbons, fatty esters, etc. For purposes of the instant disclosure, "fatty compounds" do not include fatty acids, which are separately referred to above. In addition, silicones are not considered fatty compounds according to the instant disclosure. Non-limiting examples of useful fatty compounds include oils, waxes, alkanes (paraffins), fatty acids, fatty esters, triglyceride compounds, lanolin, hydrocarbons, derivatives thereof, and mixtures thereof. Fatty compounds are described by the International Federation Societies of Cosmetic Chemists, for example, in Cosmetic Raw Material Analysis and Quality, Volume I: Hydrocarbons, Glycerides, Waxes and Other Esters (Redwood Books, 1994), which is incorporated herein by reference in its entirety.

Non-limiting examples of fatty compounds include oils, mineral oil, alkanes (paraffins), fatty acids, fatty alcohol derivatives, fatty acid derivatives, esters of fatty alcohols, hydroxy-substituted fatty acids, waxes, triglyceride compounds, lanolin, and a mixture thereof.

Fatty Alcohol Derivatives

In an embodiment, the fatty compounds include one or more fatty alcohol derivatives, which are different from fatty alcohols (component (d)). Fatty alcohol derivatives include fatty esters derived from one or more fatty alcohols. Fatty alcohol derivatives also include alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Acids

In an embodiment, fatty compounds are chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

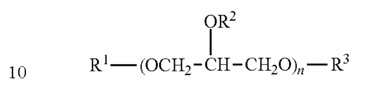

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Waxes

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Oils

In some instances, the fatty compounds may include or be chosen from one or more oil(s). Suitable oils include, among others, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the cosmetic compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

In some embodiments, the cosmetic composition may include one or more fatty compounds chosen from fatty esters (such as isononyl isononanoate), polyolefins (such as petrolatum), waxes, squalane, squalene, hydrogenated polyisobutene, hydrogenated polydecene, polybutene, mineral oil, pentahydrosqualene, plant and/or vegetable oil, hydrocarbon-based oils (such as isohexadecane), or a mixture thereof.

The total amount of the one or more fatty compounds in the cosmetic compositions will vary. Nonetheless, in various embodiment, the total amount of the one or more fatty compounds is from about 5 wt. % to about 20 wt. %, based on the total weight of the cosmetic composition. In further embodiments, the total amount of the one or more fatty compounds in the cosmetic compositions is from about 5 to 15 wt. %, about 5 to about 12 wt. %, about 6 to about 20 wt. %, about 6 to about 15 wt. %, about 6 to about 12 wt. %, based on the total weight of the cosmetic composition.

(h) Thickening Polymers

The cosmetic composition of the instant disclosure may optionally include one more thickening polymer(s). Nonlimiting examples of various types of thickening polymers include taurate copolymer, polyacrylate, polymethacrylate, polyethylacrylate, polyacrylamide, poly C10-30 alkyl acrylate, acrylic acid/acrylonitrogens copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer, carbomers, hydrophobically modified polypolyacrylates; hydrophobically modified polyacrylic acids, hydrophobically modified polyacrylamides; hydrophobically modified polyethers wherein these materials may have a hydrophobe that can be selected from cetyl, stearyl, oleayl, and combinations thereof, acrylamide/ammonium acrylate copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; sodium carbomer, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyimide-3, polyquaternium-37, sodium polyacrylate, and a mixture thereof.

Among the nonionic thickening polymers examples include:

(1) Celluloses modified with groups comprising at least one fatty chain; examples that may be mentioned include: hydroxyethylcelluloses modified with groups comprising at least one fatty chain, such as alkyl, arylalkyl or alkylaryl groups, or mixtures thereof, and in which the alkyl groups are preferably C8-C22, for instance the product NATROSOL PLUS GRADE 330 CS ($C_{16}$ alkyls) sold by the company Aqualon, or the product BERMOCOLL EHM 100 sold by the company Berol Nobel; and hydroxyethylcelluloses modified with alkylphenyl polyalkylene glycol ether groups, such as the product AMERCELL POLYMER HM-1500 (polyethylene glycol (15) nonylphenyl ether) sold by the company Amerchol, (2) Hydroxypropyl guars modified with groups comprising at least one fatty chain, such as the product ESAFLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhone-Poulenc, (3) Copolymers of vinylpyrrolidone and of fatty-chain hydrophobic monomers; examples that may be mentioned include: the products ANTARON V216 or GANEX V216 (vinylpyrrolidone/hexadecene copolymer) sold by the company I.S.P. the products ANTARON V220 or GANEX V220 (vinylpyrrolidone/eicosene copolymer) sold by the company I.S.P., (4) Copolymers of $C_1$-$C_6$ alkyl methacrylates or acrylates and of amphiphilic monomers comprising at least one fatty chain, for instance the oxyethylenated methyl acrylate/stearyl acrylate copolymer sold by the company Goldschmidt under the name ANTIL 208, (5) Copolymers of hydrophilic methacrylates or acrylates and of hydrophobic monomers comprising at least one fatty chain, for instance the polyethylene glycol methacrylate/lauryl methacrylate copolymer, (6) Polyurethane polyethers comprising in their chain both hydrophilic blocks usually of polyoxyethylenated nature and hydrophobic blocks, which may be aliphatic sequences alone and/or cycloaliphatic and/or aromatic sequences.

In a preferred embodiment, the cosmetic composition includes one or more taurate copolymers. These copolymers can act as gelling agents, thickeners, and provide emulsification properties. In particular, the inventors discovered that taurate copolymers are particularly effective for stabilizing the cosmetic compositions of the instant disclosure.

Nonlimiting examples taurate copolymers include acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof The taurate copolymers may be hydrophilic and may contain an acrylate component. The at least one taurate copolymer may include, for example, acrylamide/sodium acryloyl dimethyl taurate copolymer, hydroxyethyl acrylate/sodium acryloyl dimethyl taurate copolymer, and/or sodium acrylate/sodium acryloyl dimethyl taurate copolymer. In some instances, at least one taurate copolymer is obtainable from ethylenically unsaturated, sulpho-functional monomers and ethylenically unsaturated hydrophilic monomers, for example from crosslinked anionic copolymers of acrylamide or methacrylamide and of 2-acrylamido-2-methylpropanesulfonic acid.

In some instances, the one or more taurate copolymers may be chosen from acrylamide/sodium acryloyl dimethyl taurate copolymer, hydroxyethyl acrylate/sodium acryloyl dimethyl taurate copolymer, ammonium acryloyldimethyl taurate/VP copolymer, and mixtures thereof. Furthermore, in some instances, the cosmetic compositions may include both hydroxyethyl acrylate/sodium acryloyl dimethyl taurate copolymer and ammonium acryloyldimethyl taurate/VP copolymer, and optionally further include poly C10-30 alkyl acrylate.

Generally, the amount of the one or more thickening polymers will vary depending on the type of thickening polymers used; and depending on the desired viscosity of the cosmetic composition. Therefore, in an embodiment, the total amount of the one or more thickening agents is sufficient to achieve the viscosities set forth throughout the instant disclosure. Nonetheless, in various embodiments, the total amount of the one or more thickening polymers may range from about 1 to about 8 wt. %, based on the total weight of the cosmetic composition. In various embodiments, the amount of the one or more thickening polymers may range from about 1 to about 6 wt %, from about 1 to about 5 wt %, from about 1 to about 3 wt %, based on the total weight of the cosmetic composition.

(i) 4-tert-Butylcyclohexanol

The cosmetic compositions of the instant disclosure do not require nor do they necessarily include 4-tert-butylcyclohexanol—it is optional. Nonetheless, in various embodiments it is preferably to include 4-tert-butylcyclohexanol. 4-tert-butylcyclohexanol may be in a cis configuration, a trans configuration, or a mixture of cis and trans configurations. Among other things, 4-tert-butylcyclohexanol is useful for reducing skin irritation, for soothing the skin, and/or for reducing or alleviating stinging, burning, and tightness.

The total amount of the 4-tert-butylcyclohexanol will vary. Nonetheless, in various embodiments, the total amount of the 4-tert-butylcyclohexanol in the cosmetic composition is from about 0.1 wt. % to about 5 wt. % based on the total weight of the cosmetic composition. In further embodiments, the total amount of the 4-tert-butylcyclohexanol is from about from about 0.1 to about 4 wt %, about 0.1 to about 3 wt. %, about 0.1 to about 2 wt. %, about 0.5 to about 5 wt. %, about 0.5 to about 4 wt. %, about 0.5 to about 3 wt. %, about 0.5 to about 2 wt. %, about 1 to about 5 wt. %, about 1 to about 4 wt. %, about 1 to about 3 wt. %, or about 1 to about 2 wt. %, based on the total weight of the cosmetic composition.

(j) Water-Soluble Solvents

The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvents have a solubility of at least 60%, 70%, 80%, or 90%. Non-limiting examples of one or more water-soluble solvents are chosen from glycerin, mono-alcohols, polyols (polyhydric alcohols), glycols, and a mixture thereof.

As examples of organic solvents, non-limiting mentions can be made of monoalcohols and polyols such as ethyl alcohol, isopropyl alcohol, propyl alcohol, isopropyl alcohol, benzyl alcohol, 4-tert-butylcyclohexanol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are also useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some instances, the cosmetic compositions of the instant disclosure include one or more glycols and/or one or more alcohols, for example, one or more water-soluble solvents selected from the group consisting of propylene glycol, butylene glycol, pentylene glycol, ethanol, isopropanol, tert-butyl alcohol, and mixtures thereof.

The total amount of the one or more water-soluble solvents will vary. Nonetheless, in various embodiments, the total amount of the one or more water-soluble is from about 0.1 to about 20 wt. %, based on the total weight of the cosmetic composition. In further embodiments, the total amount of the one or more water-soluble solvents is about 0.1 to about 20 wt. %, about 0.1 to about 15 wt. %, about 0.1 to about 10 wt. %, about 0.1 to about 5 wt. %, from about 0.1 wt % to about 1 wt %, about 2 to about 20 wt. %, about 2 to about 15 wt. %, about 2 to about 10 wt. %, about 2 to about 5 wt. %, about 5 to about 20 wt. %, about 5 to about 15 wt. %, or about 5 to about 10 wt. %, based on the total weight of the cosmetic composition.

(k) Silicones

In an embodiment, the composition includes one or more silicones. Nonetheless, silicones are not required are necessarily present. Therefore, in certain embodiments, they may be excluded from the cosmetic compositions. In other embodiments, it is preferable to include one or more silicones. Nonlimiting examples of silicones include dimethicone, dimethiconol, cyclomethicone, polysilicone-11, phenyl trimethicone, trimethylsilylamodimethicone, and stearoxytrimethylsilane. In some instances, the one or more silicones are non-volatile silicon oils. In some embodiments, the silicone is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl (trimethylsiloxy)diphenylsiloxanes, diphenyl dimethicones, diphenyl(methyldiphenyl)trisiloxanes or (2-phenylethyl) trimethylsiloxysilicates. Other examples of silicone that may be mentioned include volatile linear or cyclic silicones, such as those with a viscosity 8 centistokes (8×106 m2/s) and/or containing from 2 to 7 silicon atoms. These silicones optionally comprise alkyl or alkoxy groups containing from 1 to 10 carbon atoms. Non-limiting examples of volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, or mixtures thereof.

In a preferred embodiment, the cosmetic compositions include one or more silicones chosen from dimethicone, dimethiconol, cyclomethicone, polysilicone-11, phenyl trimethicone, and amodimethicone, preferably dimethicone.

In some instances, the cosmetic compositions include one or more amino functionalized silicones. Nonlimiting examples include amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. Amodimethicone is a particularly useful amino functionalized silicone.

The total amount of silicones in the cosmetic composition, if present, will vary. Nonetheless, in various embodiments, the amount of silicones in the cosmetic composition is about 0.01 to about 15 wt. %, about 0.01 to about 10 wt. %, about 0.01 to about 5 wt. %, about 0.01 to about 3 wt. %, about 0.01 to about 2 wt. %, about 0.1 to about 15 wt. %, about 0.1 to about 10 wt. %, about 0.1 to about 5 wt. %, about 0.1 to about 3 wt. %, about 0.1 to about 2 wt. %, based on the total weight of the cosmetic composition.

(l) Miscellaneous Ingredients

The cosmetic compositions of the instant disclosure may optionally include one or more miscellaneous ingredients. Miscellaneous ingredients are ingredients that are compatible with the cosmetic compositions and do not disrupt or materially affect the basic and novel properties of the cosmetic compositions. Miscellaneous ingredients commonly used in cosmetics are known in the art. Non-limiting examples include miscellaneous emulsifiers/surfactants other than those of (c), (d), and (e), preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, colorants, mattifying agents, further skin active agents, depigmenting agents, anti-wrinkle agents, etc. In a preferred embodiment, the cosmetic compositions of the instant disclosure include one or more skin active agents, in particular, madecassoside. Nonlimiting examples of various miscellaneous ingredients that may optionally be include (or excluded) from the cosmetic compositions is provided below.

Miscellaneous Emulsifiers/Surfactants

Miscellaneous emulsifiers/surfactants may optionally be included in the cosmetic compositions. Miscellaneous emulsifiers/surfactants are those that are not: (c) nonionic emulsifier chosen from glyceryl esters having an HLB of about 3 to about 8; (d) nonionic emulsifiers having an HLB of about 16 to about 18; and (e) nonionic emulsifiers having an HLB of about 9 to about 15. The miscellaneous emulsifiers/surfactants may be nonionic, anionic, cationic, and/oramphoteric/zwitterionic.

Antioxidants

Examples of antioxidants include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ.-tocotrienol, d-delta-tocotrienol,) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, *Emblica officinalis*, and bioflavonoids from rose hip and citrus may be used including water soluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E, and other carotenoids.

Flavonoids can also function as antioxidants. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcum in, bis-Desmethoxycurcum in, Tetrahydrocurcum in, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (*Sesamum indicum*) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

Skin Active Agents

Nonlimiting examples of skin active agents include madecassoside, sodium hyaluronate, retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate; —derivatives particularly copper and copper pidolate as Cuivridone Solabia—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of Terminalia chebula, nasturtium and of bioavailable zinc (microalgae), such as that sold under the name Seborilys Green Tech; —extracts of Pygeum afrianum such as that sold under the name Pygeum afrianum sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *Laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of *Cinchona* bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

Depigmenting Agents

Nonlimiting examples of depigmenting agents include alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, certain compounds derived from plants such as chamomile, bearberry, the aloe family (*vera, ferox*, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

Anti-Wrinkle Agent

The term “anti-wrinkle agent” refers to a natural or synthetic compound producing a biological effect, such as the increased synthesis and/or activity of certain enzymes, when brought into contact with an area of wrinkled skin, this has the effect of reducing the appearance of wrinkles and/or fine lines. Nonlimiting examples of anti-wrinkle agents include: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinoids other than retinol (as discussed above, such as retinol palmitate), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *Laminaria*, bacterial extracts, the sapogenins such as diosgenin and extracts of *Dioscorea* plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof. In at least one case, the skin tightening composition includes adenosine derivatives, such as non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl (“PIA”), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

Miscellaneous ingredients can optionally be included in the cosmetic composition and if present, the amount will vary. Nonetheless, in various embodiments the total amount of the one or more miscellaneous ingredients is from about 0.01 to about 10 wt. %, based on the total weight of the cosmetic composition. In further embodiments, the total amount of the one or more miscellaneous ingredients is from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 1 to about 10 wt. %, about 1 to about 8 wt. %, about 1 to about 5 wt. %, or about 1 to about 3 wt. %, based on the total weight of the cosmetic composition.

As already noted, skin active agents may be included as one or more of the miscellaneous ingredients. With respect to the total amount of skin active agents in the cosmetic compositions, if present, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; about 0.1 to about 10 wt. %, about 0.1 to about 5 wt. %, about 0.1 to about 2.5 wt. %, about 0.1 to about 1 wt. %, about 0.1 to about 0.5 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, or about 4 to about 6 wt. %, based on the total weight of the cosmetic composition.

pH

In an embodiment, the cosmetic compositions have a pH of about 4 to about 8. In further embodiments, the pH of the cosmetic compositions is from 4.5 to about 8, about 5 to about 8, about 5.5 to about 8, about 4 to about 7.5, about 4 to about 7, about 4.5 to about 8, about 4.5 to about 7.5, about 4.5 to about 7, about 5 to about 8, about 5 to about 7.5, or about 5 to about 7. In various embodiments, the pH of the cosmetic compositions does not change by more than ±1 pH unit, ±0.5 pH units, ±0.3 pH units, or ±0.2 pH units, for at least 2 weeks, 4 weeks, and/or 8 weeks in storage at 4° C., 25° C., 37° C., and/or 45° C.

Stability

The cosmetic compositions of the instant disclosure are stable. For example, the cosmetic compositions do not visually phase separate or form visibly observable particulates for at least 2 weeks, 4 weeks, and/or 8 weeks in storage at 4° C., 25° C., 37° C., and/or 45° C.

In various embodiments, the cosmetic compositions do not visually phase separate or form visibly observable particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C.

In various embodiments, the viscosity of the cosmetic compositions does not change by more than 20%, 15%, 10%, or 5%, for at least 2 weeks, 4 weeks, and/or 8 weeks in storage at 4° C., 25° C., 37° C., and/or 45° C.

Viscosity

In general, the cosmetic compositions of the instant case have a viscosity of about 5,000 to about 200,000 Pa·s at 25° C., and shear rate of 1 $s^{-1}$ at 25° C. However, the cosmetic compositions may have a viscosity of about 10,000 to about 200,000 Pa·s, about 10,000 to about 180,000 Pa·s, about 10,000 to about 150,000 Pa·s, about 10,000 to about 120,000 Pa·s, about 15,000 to about 200,000 Pa·s, about 15,000 to about 180,000 Pa·s, about 15,000 to about 150,000 Pa·s, about 15,000 to about 120,000 Pa·s, about 20,000 to about 200,000 Pa·s, about 20,000 to about 180,000 Pa·s, about 20,000 to about 150,000 Pa·s, or about 20,000 to about 120,000 Pa·s at 25° C., and shear rate of 1 $s^{-1}$ at 25° C.

The viscosity measurements can be carried out, for example, using a Brooksfield viscometer/rheometer using a t-bar spindle at a speed of 5, 10, 15, and/or 20 rpm. An RVDV-II+Pro Viscometer with RheocalcT software may be employed for automated instrument control and data acquisition. The test temperature is maintained at 25° C. by using a Brookfield TC-502P Programmable Refrigerated Bath. From its original container, a sample is transferred into a 120 mL glass jar and then tested.

Methods

The instant disclosure relates to methods of treating skin. The methods include applying a cosmetic composition according to the instant disclosure, optionally allowing the cosmetic composition to remain on the skin for a period of time. The cosmetic compositions are typically applied directly to the skin using the hand or a cloth. The skin may be optionally washed or rinsed prior to application. The method for treating the skin can be carried out once daily or may be carried out multiple times. For example, the method for treating skin may be carried out once daily, twice daily, weekly, bi-weekly for an extended period of time, for example, for about 1, 2, 3, 4, 5, or 6 months up to 1 year, or longer. In an embodiment, the methods reduce the appearance of fine lines and wrinkles, improve production of hyaluronic acid via stimulation of glycosaminoglycan (GAG) synthesis, thereby softening of stratum corneum to relieve cumulative stress on the epidermis and dermis, etc. When tert-butylcyclohexanol is included in the compositions, the methods further treat skin irritation, sooth the skin, and/or reduce or alleviate stinging, burning, and tightness.

The instant disclosure also relates to methods for stabilizing cosmetic composition containing high amounts of hydroxypropyl tetrahydropyrantriol, and optionally high amounts of 4-tert-butylcyclohexanol, if present. These methods comprises incorporating hydroxypropyl tetrahydropyrantriol, and optionally 4-tert-butylcyclohexanol, into the compositions of the instant disclosure. The amounts of hydroxypropyl tetrahydropyrantriol and 4-tert-butylcyclohexanol that may be incorporated are the amounts set forth throughout the instant disclosure.

Kits

The cosmetic compositions of the instant disclosure may be provided in a kit, for example, a kit comprising an individually contained cosmetic composition according to the instant disclosure and one or more additional separately contained cosmetic compositions. In an embodiment, the one or more separately contained compositions may be an additional composition according to the instant disclosure or may be a different composition. The cosmetic compositions may be separately contained in different cartridges, which are included in a dispensing apparatus/device. In other words, the kit may be a dispensing apparatus/device comprising a plurality of cartridges in which the compositions are contained. The kit (or apparatus/device) may optionally dispense the cosmetic composition of the instant disclosure and separately dispense the one or more separately contained composition. In various embodiments, the compositions may be dispensed individually or concurrently, and may optionally be mixed (or not mixed) with each other prior to being dispensed. In an embodiment, the various compositions are not mixed with each other prior to being dispensed. Useful systems, cartridges, and dispensing apparatus/devices are disclosed in U.S. Pat. Nos. 9,968,177 and 9,808,071; US Patent Application Publication. Nos. 2021/0236390, 2021/0235849 and 2021/0236863; and in U.S. Ser. No. 17/162,555, which are all incorporated herein by reference in their entirety.

EMBODIMENTS

In some embodiments, the cosmetic composition comprises or consists of:

(a) about 10 to about 40 wt. %, preferably about 10 to about 20 wt. %, more preferably about 12 to about 18 wt. % of hydroxypropyl tetrahydropyrantriol;

(b) about 50 to about 85 wt. %, preferably about 55 to about 80 wt. %, more preferably about 55 to about 75 wt. % of water;

(c) about 0.1 to about 5 wt. %, preferably about 0.1 to about 4, more preferably about 0.2 to about 3 wt. % of one or more nonionic emulsifiers chosen from glyceryl esters having an HLB of about 3 to about 8, for example, glyceryl esters chosen from, glyceryl behenate, glyceryl erucate, glyceryl hydroxystearate, glyceryl lanolate, glyceryl laurate, glyceryl myristate, glyceryl palmitate lactate, glyceryl stearate, glyceryl distearate, glyceryl laurate, and a mixture thereof, preferably one or more glyceryl esters chosen from glyceryl stearate, glyceryl ricinoleate, and a mixture thereof;

(d) about 0.1 to about 5 wt. %, preferably about 0.1 to about 4, more preferably about 0.2 to about 3 wt. % of one or more nonionic emulsifiers having an HLB of about 16 to about 18, preferably one or more ethoxylated emulsifiers chosen from ethoxylated fatty acids, ethoxylated sorbitan fatty esters, and a mixture thereof, preferably one or more ethoxylated fatty acids;

(e) about 0.1 to about 5 wt. %, preferably about 0.5 to about 5 wt. %, more preferably about 0.5 to about 4 wt. % of one or more nonionic emulsifiers having an HLB of about 9 to about 15, for example, chosen from alkylpolyglucosides (cetearyl glucoside), polyglycerol-based emulsifiers (polygyceryl-3 methylglucose distearate), sorbitan fatty esters (polysorbate 60), sugar esters or ethers, sugar-based esters or ethers, polyol fatty esters or ethers, glyceryl fatty esters or ethers, ethoxylates thereof, or mixtures thereof, preferably chosen from sugar esters or ethers and sugar-based esters or ethers;

(f) about 1 to about 10 wt. %, preferably about 1 to about 8 wt. %, more preferably about 1 to about 6 wt. % of one or more fatty alcohols, preferably chosen from fatty alcohols having from 8 to 24 carbon atoms, preferably chosen from cetyl alcohol, stearyl alcohol, cetearyl alcohol, behenyl alcohol, lauryl alcohol, myristic or myristyl alcohol, arachidyl alcohol, lignoceryl alcohol, and mixtures thereof;

(g) about 5 to about 20 wt. %, preferably about 5 to about 15 wt. %, more preferably about 6 to about 12 wt. % of one or more fatty compounds, for example, chosen from fatty esters (e.g., isononyl isononanoate), polyolefins (petrolatum), waxes, squalane, squalene, hydrogenated polyisobutene, hydrogenated polydecene, polybutene, mineral oil, pentahydrosqualene, plant and/or vegetable oil (e.g., soybean oil), hydrocarbon-based oils (e.g., isohexadecane), and a mixture thereof;

(h) one or more thickening polymers, preferably one or more taurate copolymers, in particular, one or more taurate copolymers chosen from acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof, wherein the amount of the one or more thickening polymers may optional be from about 1 to about 8 wt. %, preferably about 1 to about 5 wt. %, more preferably about 1 to about 3 wt. %;

(i) optionally, 4-tert-butylcyclohexanol, wherein if present is preferably in an amount of about 0.1 to about 5 wt. %, preferably about 0.5 to about 4 wt. %, more preferably, 0.5 to about 3 wt. %;

(j) optionally, one or more water-soluble solvents, for example, one or more water-soluble solvents chosen glycerin, alcohols (for example, C1-30, C1-15, C1-10, or C1-4 alcohols), organic solvents, polyols (polyhydric alcohols, e.g., ethanol, isopropanol, t-butyl alcohol, etc.), glycols (e.g., propylene glycol, butylene glycol, pentylene glycol, etc.), and a mixture thereof, preferably one or more monoalcohols chosen from ethanol, isopropanol, and t-butyl alcohol, and one or more glycols chosen from propylene glycol, butylene glycol, and pentylene glycol, wherein if present, the one or more water-soluble solvents comprise about 0.1 to about 20 wt. %, preferably about 0.1 to about 15 wt. %, more preferably about 1 to about 15 wt. % of the cosmetic composition;

(k) optionally, one or more silicones, for example, dimethicone, dimethiconol, cyclomethicone, polysilicone-11, phenyl trimethicone, and amodimethicone, preferably dimethicone, wherein if present, the one or more silicones may be in an amount of about 0.01 to about 10 wt. %, about 0.1 to about 5 wt. %, more preferably about 0.1 to about 3 wt. %;

(l) optionally, one or more miscellaneous ingredients, for example, one or more miscellaneous ingredients chosen from miscellaneous emulsifiers/surfactants, preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, colorants, mattifying agents, further skin active agents, depigmenting agents, anti-wrinkle agents, wherein if present, the one or more miscellaneous ingredients comprise about 0.01 to about 0.1 to about 10 wt. %, preferably about 0.1 to about 8 wt. %, more preferably about 1 to about 8 wt. % of the cosmetic composition wherein the composition is an oil in water emulsion, preferably a gel emulsion, and all percentages by weight are based on the total weight of the cosmetic composition.

The composition preferably has a pH of about 4 to about 8, preferably about 5 to about 8, more preferably about 4.5 to about 7.5.

The cosmetic compositions of the instant disclosure are stable. For example, in an embodiment the cosmetic compositions do not visually phase separate or form visibly observable particulates for at least 2 weeks, 4 weeks, and/or 8 weeks in storage at 4° C., 25° C., 37° C., and/or 45° C.

In another embodiment, the cosmetic compositions do not visually phase separate or form visibly observable particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C.

In an embodiment, the viscosity of the cosmetic compositions does not change by more than 20%, 15%, 10%, or 5%, for at least 2 weeks, 4 weeks, and/or 8 weeks in storage at 4° C., 25° C., 37° C., and/or 45° C.

In certain embodiments, the cosmetic composition preferably has a viscosity of about 5,000 to about 200,000 Pa·s at 25° C., and shear rate of 1 $s^{-1}$ at 25° C. However, the cosmetic compositions may have a viscosity of about 10,000 to about 200,000 Pa·s, about 10,000 to about 180,000 Pa·s, about 10,000 to about 150,000 Pa·s, about 10,000 to about 120,000 Pa·s, about 15,000 to about 200,000 Pa·s, about 15,000 to about 180,000 Pa·s, about 15,000 to about 150,000 Pa·s, about 15,000 to about 120,000 Pa·s, about 20,000 to about 200,000 Pa·s, about 20,000 to about 180,000 Pa·s, about 20,000 to about 150,000 Pa·s, or about 20,000 to about 120,000 Pa·s at 25° C., and shear rate of 1 $s^{-1}$ at 25° C.

In some embodiments, the cosmetic composition comprises or consists of:

(a) about 10 to about 40 wt. %, preferably about 10 to about 20 wt. %, more preferably about 12 to about 18 wt. % of hydroxypropyl tetrahydropyrantriol;

(b) about 50 to about 85 wt. %, preferably about 55 to about 80 wt. %, more preferably about 55 to about 75 wt. % of water;

(c) about 0.1 to about 5 wt. %, preferably about 0.1 to about 4, more preferably about 0.2 to about 3 wt. % of one or more nonionic emulsifiers chosen from glyceryl esters having an HLB of about 3 to about 8, in particular chosen from glyceryl stearate, glyceryl ricinoleate, and a mixture thereof, preferably glyceryl stearate;

(d) about 0.1 to about 5 wt. %, preferably about 0.1 to about 4, more preferably about 0.2 to about 3 wt. % of one or more nonionic emulsifiers having an HLB of about 16 to about 18 chosen from ethoxylated fatty acids, ethoxylated sorbitan fatty esters, and a mixture thereof, preferably one or more ethoxylated fatty acids;

(e) about 0.1 to about 5 wt. %, preferably about 0.5 to about 5 wt. %, more preferably about 0.5 to about 4 wt. % of one or more nonionic emulsifiers having an HLB of about 9 to about 15, for example, chosen from alkylpolyglucosides (cetearyl glucoside), polyglycerol-based emulsifiers (polygyceryl-3 methylglucose distearate), sorbitan fatty esters (polysorbate 60), sugar esters or ethers, sugar-based esters or ethers, polyol fatty esters or ethers, glyceryl fatty esters or ethers, ethoxylates thereof, or mixtures thereof, preferably chosen from sugar esters or ethers and sugar-based esters or ethers;

(f) about 1 to about 10 wt. %, preferably about 1 to about 8 wt. %, more preferably about 1 to about 6 wt. % of one or more fatty alcohols having from 8 to 24 carbon atoms, preferably chosen from cetyl alcohol, cetearyl alcohol, behenyl alcohol, and mixtures thereof;

(g) about 5 to about 20 wt. %, preferably about 5 to about 15 wt. %, more preferably about 6 to about 12 wt. % of one or more fatty compounds, for example, chosen from fatty esters (e.g., isononyl isononanoate), polyolefins (petrolatum), waxes, squalane, squalene, hydrogenated polyisobutene, hydrogenated polydecene, polybutene, mineral oil, pentahydrosqualene, plant and/or vegetable oil (e.g., soybean oil), hydrocarbon-based oils (e.g., isohexadecane), and a mixture thereof;

(h) about 1 to about 8 wt. %, preferably about 1 to about 5 wt. %, more preferably about 1 to about 3 wt. % of one or more taurate copolymers, in particular, one or more taurate copolymers chosen from acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof, preferably chosen from hydroxyethyl acrylate/sodium acryloyldimethyl taurate copolymer, ammonium acryloyldimethyl taurate/VP copolymer, and a mixture thereof;

(i) optionally, 4-tert-butylcyclohexanol, wherein if present is preferably in an amount of about 0.1 to about 5 wt. %, preferably about 0.5 to about 4 wt. %, more preferably, 0.5 to about 3 wt. %;

(j) about 0.1 to about 20 wt. %, preferably about 0.1 to about 15 wt. %, more preferably about 1 to about 5 wt. % of, one or more water-soluble solvents chosen from one or more monoalcohols (e.g., ethanol, isopropanol, and t-butyl alcohol) one or more glycols (e.g., propylene glycol, butylene glycol, and pentylene glycol), and a mixture thereof;

(k) about 0.01 to about 10 wt. %, about 0.1 to about 5 wt. %, more preferably about 0.1 to about 3 wt. % of one or more silicones, for example, dimethicone, dimethiconol, cyclomethicone, polysilicone-11, phenyl trimethicone, and amodimethicone, preferably dimethicone;

(l) optionally, one or more miscellaneous ingredients, for example, one or more miscellaneous ingredients chosen from miscellaneous emulsifiers/surfactants, preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, colorants, mattifying agents, further skin active agents, depigmenting agents, anti-wrinkle agents, wherein if present, the one or more miscellaneous ingredients comprise about 0.01 to about 0.1 to about 10 wt. %, preferably about 0.1 to about 8 wt. %, more preferably about 1 to about 8 wt. % of the cosmetic composition wherein the composition is an oil in water emulsion, preferably a gel emulsion, and all percentages by weight are based on the total weight of the cosmetic composition.

The composition preferably has a pH of about 4 to about 8, preferably about 5 to about 8, more preferably about 4.5 to about 7.5.

The cosmetic compositions of the instant disclosure are stable. For example, in an embodiment the cosmetic compositions do not visually phase separate or form visibly observable particulates for at least 2 weeks, 4 weeks, and/or 8 weeks in storage at 4° C., 25° C., 37° C., and/or 45° C.

In another embodiment, the cosmetic compositions do not visually phase separate or form visibly observable particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C.

In an embodiment, the viscosity of the cosmetic compositions does not change by more than 20%, 15%, 10%, or 5%, for at least 2 weeks, 4 weeks, and/or 8 weeks in storage at 4° C., 25° C., 37° C., and/or 45° C.

In certain embodiments, the cosmetic composition preferably has a viscosity of about 5,000 to about 200,000 Pa·s at 25° C., and shear rate of 1 $s^{-1}$ at 25° C. However, the cosmetic compositions may have a viscosity of about 10,000 to about 200,000 Pa·s, about 10,000 to about 180,000 Pa·s, about 10,000 to about 150,000 Pa·s, about 10,000 to about 120,000 Pa·s, about 15,000 to about 200,000 Pa·s, about 15,000 to about 180,000 Pa·s, about 15,000 to about 150,000 Pa·s, about 15,000 to about 120,000 Pa·s, about 20,000 to about 200,000 Pa·s, about 20,000 to about 180,000 Pa·s, about 20,000 to about 150,000 Pa·s, or about 20,000 to about 120,000 Pa·s at 25° C., and shear rate of 1 $s^{-1}$ at 25° C.

EXAMPLES

As various changes could be made in the above-described methods without departing from the scope of the invention, it is intended that all matter contained in the above description and in the examples given below, shall be interpreted as illustrative and not in a limiting sense.

The following Examples are intended to be non-restrictive and explanatory only. The ingredient amounts in the compositions/formulas described below are expressed in % by weight, based on the total weight of the composition.

Example 1

Inventive Compositions

| | | | A | B | C | D |
|---|---|---|---|---|---|---|
| (a) | Active | HYDROXYPROPYL TETRAHYDROPYRANTRIOL | 15 | 15 | 15 | 15 |
| (b) | Water | WATER | 63.5 | 63.9 | 63.5 | 63.9 |
| (c) | Glyceryl Ester | GLYCERYL STEARATE (HLB 3.8 ± 1) | 0.3 | 0.3 | 0.3 | 0.3 |
| (d) | High HLB Emulsifier | PEG-40 STEARATE (HLB 17.5) | 0.4 | 0.4 | 0.4 | 0.4 |
| (e) | Mid-HLB Emulsifer | POLYGLYCERYL-3 METHYLGLUCOSE DISTEARATE (HLB-12) | 0.5 | 0.5 | 0.5 | 0.5 |
| | | CETEARYL GLUCOSIDE (HLB 11 ± 1) | 0.2 | 0.2 | 0.2 | 0.2 |
| | | POLYSORBATE 60 (HLB 14.9 ± 1) | 0.04 | 0.04 | 0.04 | 0.04 |
| (f) | Fatty Alcohol | CETYL ALCOHOL | 0.3 | 0.3 | 0.8 | 0.8 |
| | | BEHENYL ALCOHOL | 1.0 | 1.0 | 1.0 | 1.0 |
| | | CETEARYL ALCOHOL | 0.8 | 0.8 | 0.3 | 0.3 |
| (g) | Fatty Compound | SQUALANE, ISONONYL ISONONANOATE, AND SOYBEAN OIL | 9 | 9 | 9 | 9 |
| (h) | Thickening Polymers | HYDROXYETHYL ACRYLATE/SODIUM ACRYLOYLDIMETHYL TAURATE COPOLYMER | 0.7 | 0.7 | 0.7 | 0.7 |
| | | AMMONIUM ACRYLOYLDIMETHYLTAURATE/VP COPOLYMER | 0.7 | 0.7 | 0.7 | 0.7 |
| | | POLY C10-30 ALKYL ACRYLATE | 0.5 | 0.5 | 0.5 | 0.5 |
| (i) | Active | 4-T-BUTYLCYCLOHEXANOL | 1.1 | 1.1 | 1.1 | 1.1 |
| (j) | Water-Soluble Solvent | PROPYLENE GLYCOL, PENTYLENE GLYCOL, AND T-BUTYL ALCOHOL | 4.2 | 4.2 | 4.2 | 4.2 |
| (k) | Silicone | DIMETHICONE | 0.5 | 0.5 | 0.5 | 0.5 |
| (l) | Miscellaneous Emulsifiers | SORBITAN ISOSTEARATE (HLB 4.7) | 0.04 | 0.04 | 0.04 | 0.04 |
| | | HYDROGENATED LECITHIN | 0.3 | | 0.3 | |
| Other miscellaneous emulsifiers/surfactants, Salts, Preservatives, pH Adjusters, Fragrances, Colorants, Chelants, Extracts, Fillers, Absorbants, Additional Skin Actives, etc. | | | ≤4 | ≤4 | ≤4 | ≤4 |
| Stability | | | Yes | Yes | Yes | Yes |

Example 2

Comparative Compositions

| | | | C-1 | C-2 | C-3 |
|---|---|---|---|---|---|
| (a) | Active | HYDROXYPROPYL TETRAHYDROPYRANTRIOL | 15 | 15 | 15 |
| (b) | Water | WATER | 69.5 | 61.5 | 55.8 |
| (c) | Glyceryl Ester | GLYCERYL STEARATE (HLB = 3.8) | | 1.6 | |
| (d) | High HLB | STEARETH-100 (HLB = 18.8) | 0.4 | | |
| (e) | Mid-HLB Emulsifiers | ARACHIDYL GLUCOSIDE (HLB ~10) | | | |
| | | C12-20 ALKYL GLUCOSIDE (HLB = 10.3) | | | 0.4 |
| | | CETEARYL GLUCOSIDE (HLB = 11) | 0.1 | | |
| | | POLYSORBATE 80 (HLB = 15) | | 0.2 | |
| | | POLYSORBATE 60 (HLB = 14.9) | | 0.04 | |
| (f) | Fatty Alcohols | ARACHIDYL ALCOHOL, BEHENYL ALCOHOL, CETEARYL ALCOHOL, CETYL ALCOHOL, AND/OR C14-22 ALCOHOLS | 3.2 | 1.1 | 4.1 |
| (g) | Fatty Compounds | SQUALANE. SOYBEAN OIL, ISONONYL ISONONANOATE, ISOHEXADECANE, DICAPRYLYL ETHER, AND/OR CAPRYLIC/CAPRIC TRIGLYCERIDE | 2 | 9.5 | 4 |
| (h) | Thickening Polymers | ACRYLAMIDE/SODIUM ACRYLOYLDIMETHYLTAURATE COPOLYMER | | 1 | |
| | | HYDROXYETHYL ACRYLATE/SODIUM ACRYLOYLDIMETHYL TAURATE COPOLYMER | | 0.7 | |
| | | AMMONIUM ACRYLOYLDIMETHYLTAURATE/VP COPOLYMER | | 1.2 | |
| | | SODIUM POLYACRYLATE | 1.3 | | |
| | | XANTHAN GUM | | | 0.3 |
| | | POLYACRYLATE CROSSPOLYMER-6 | | | 0.8 |
| | | ALUMINUM STARCH OCTENYLSUCCINATE | 1 | | 1 |
| (i) | Active | 4-T-BUTYLCYCLOHEXANOL | 1.1 | 1.1 | 1.1 |
| (j) | Water-Soluble Solvent | T-BUTYL ALCOHOL, CAPRYLYL GLYCOL, PENTYLENE GLYCOL, AND/OR PROPYLENE GLYCOL | 4.5 | 4.2 | 13.5 |
| (k) | Silicone | DIMETHICONE | | | 0.5 |
| (l) | Miscellaneous Emulsifiers | SORBITAN ISOSTEARATE (HLB = 4.7) | | 0.04 | 0.3 |
| | | SORBITAN OLEATE (HLB = 4.3) | | 0.1 | |
| | | DISODIUM ETHYLENE DICOCAMIDE PEG-15 DISULFATE | | 0.5 | |
| | | Other Miscellaneous emulsifiers/surfactants, Salts, Preservatives, pH Adjusters, Fragrances, Colorants, Chelants, Extracts, Fillers, Absorbants, and/or Additional Skin Actives, etc. | ≤4 | ≤4 | ≤4 |
| | | Stability | NO | NO | NO |

Example 3

The compositions of Example 1 and Example 2 were subjected to stability studies and visually evaluated for phase separation and assessed under a microscope for particulate formation. The compositions were analyzed upon initial manufacture of the composition (To). The compositions were again analyzed after 10 days of freeze-thaw testing. For freeze-thaw testing, the compositions were placed in a stability chamber and subjected to temperature fluctuation at 12-hour intervals. For 12 hours, the compositions were held at −20° C. For the next 12 hours, the compositions were held at 25° C. The cycle was repeated 10 times (for 10 days). Separately, the compositions of Example 1 were evaluated after 4 weeks (1 month) in storage at 4° C., 25° C., 37° C., and 45° C. and again at 8 weeks (2 months) at 4° C., 25° C., 37° C., and 45° C. and visually evaluated for phase separation and assessed under a microscope for particulate formation.

The inventive compositions were deemed stable ("Y") (yes) because they did not visually phase separate and did not form particulates. The Comparative Compositions (C-1 through C-3) were deemed not stable ("N") (no) because they phase separated and/or formed particulates. The data show the importance of the one or more nonionic emulsifier chosen from glyceryl esters having HLB of about 3 to about 8 (c) and the importance of the one or more nonionic emulsifiers having an HLB of about 16 to about 18 (d). If one of these types of emulsifiers is not included, the resulting composition lacks stability, i.e., exhibits phase separation and particulate formation, as shown by the data for the Comparative Compositions (C-1, C-2, and C-3).

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

Definitions

As used herein, a "gel emulsion" is also referred to in the art as "emulsion gel." A gel emulsion is an oil in water emulsion, which is a composite structure of oil droplets within a gel matrix. They can be categorized as emulsion-filled gels and emulsion particulate gels.

The term "HLB" refers to Hydrophile-Lipophile Balance, which is a measure of the degree to which an emulsifier is hydrophilic or lipophilic, determined by calculating values for the different regions of the molecule, as described by Griffin, William C., "*Classification of Surface-Active Agents* by 'HLB'", Journal of the Society of Cosmetic Chemists, 1 (5): 311-26 (1949) and Griffin, William C., "*Calculation of HLB Values of Non-Ionic Surfactants*," Journal of the Society of Cosmetic Chemists, 5 (4): 249-56 (1954), which are incorporated herein by reference in their entirety.

"Sugar ester" as used herein means "sugar alcohol fatty acid ester" or "sugar acid fatty alcohol ester" and "sugar ether" as used herein means "sugar alcohol fatty alcohol ether".

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements chosen from A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting. Appropriate counterions for the components described herein are known in the art.

The expression "one or more" means "at least one" and thus includes individual components as well as mixtures/combinations.

The term "plurality" means "more than one" or "two or more."

An "alkyl radical" is a linear or branched saturated hydrocarbon-based group, particularly $C_1$-$C_8$, more particularly $C_1$-$C_6$, preferably $C_1$-$C_4$ such as methyl, ethyl, isopropyl and tert-butyl;

An "alkoxy radical" is a alkyl-oxy wherein alkyl is as described herein before;

An "alkenyl radical" is a linear or branched unsaturated hydrocarbon-based group, particularly $C_2$-$C_8$, more particularly $C_2$-$C_6$, preferably $C_2$-$C_4$ such as ethylenyl, propylenyl;

An "alkylene radical" is a linear or branched divalent saturated $C_1$-$C_8$, in particular $C_1$-$C_6$, preferably $C_1$-$C_4$ hydrocarbon-based group such as methylene, ethylene or propylene.

Some of the various categories of components identified for the cosmetic compositions may overlap. In such cases where overlap may exist and the composition/product includes two overlapping components (or more than two overlapping components), an overlapping component does not represent more than one component. As an example, a fatty acid may be considered both a "non-triglyceride and non-aromatic fatty emollient" and a "surfactant/emulsifier." If a particular composition/product includes both a non-triglyceride and non-aromatic fatty emollient component and an surfactant/emulsifier component, a single type of fatty acid can serve as only a non-triglyceride and non-aromatic fatty emollient or a surfactant/emulsifier (a single fatty acid does not serve as both the non-triglyceride and non-aromatic fatty emollient component and the surfactant/emulsifier component).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions may be modified with the term "about," whether or not expressly stated.

Additionally, all numbers are intended to represent exact values as additional embodiments, whether or not modified by the term "about." For example, "an amount of about 1%" can be modified to refer to exactly 1%. As a further example, "an amount of 1%" can be modified to refer to "about 1%." Unless otherwise indicated, the term "about" is understood to encompass a range of +/−10% from the stated number. However, in some embodiments, the term may be defined to encompass narrower ranges, for example, +/−1%, 2%, 3%, 4%, 5%, 6%, 7%, 8%, 9%, and 10% from the stated number.

The term "surfactants" and "emulsifiers" include salts of the surfactants and emulsifiers even if not explicitly stated. In other words, whenever the disclosure refers to a surfactant or emulsifier, it is intended that salts are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants and emulsifiers. However, additional cations such as ammonium ions, or alkanolammonium ions such as monoethanolammonium or triethanolammonium ions, may also form salts of surfactants.

The term “substantially free” or “essentially free” as used herein means the specific material may be present in small amounts that do not materially affect the basic and novel characteristics of the claimed invention. For instance, there may be less than 2% by weight of a specific material added to a composition, based on the total weight of the composition (provided that an amount of less than 2% by weight does not materially affect the basic and novel characteristics of the claimed invention). Similarly, a composition “substantially free” or “essentially free” of a stated material may include less than 1.5 wt. %, less than 1 wt. %, less than 0.5 wt. %, less than 0.1 wt. %, less than 0.05 wt. %, or less than 0.01 wt. %, or none of the specified material. The term “substantially free” or “essentially free” as used herein may also mean that the specific material is not added to the composition but may still be present in a raw material that is included in the composition.

Furthermore, all components that are positively set forth in the instant disclosure may be negatively excluded from the claims, e.g., a claimed composition may be “free,” “essentially free” (or “substantially free”) of one or more components that are positively set forth in the instant disclosure. As an example, silicones can optionally be included in the cosmetic compositions but in some instances the compositions may be free or essentially free from silicones. Silicones are synthetic polymers made up of repeating units of siloxane, elemental silicon and oxygen, combined with other elements, most often carbon and hydrogen. Thus, silicones are also called polysiloxanes. In some instances, cosmetic compositions of the instant case can be free or essentially free from dimethicones, amomdimethicones, dimethiconols, cyclosiloxanes, siloxanes, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising:

(a) about 12 to about 25 wt. % of hydroxypropyl tetrahydropyrantriol;

(b) water;

(c) about 0.1 to about 5 wt. % of one or more nonionic emulsifiers chosen from glyceryl esters having a Hydrophile-Lipophile Balance (HLB) of about 3 to about 8;

(d) about 0.1 to about 5 wt. % of one or more nonionic emulsifiers having an HLB of about 16 to about 18 chosen from ethoxylated fatty acids, ethoxylated sorbitan fatty esters, and mixtures thereof;

(e) about 0.1 to about 5 wt. % of one or more nonionic emulsifiers having an HLB of about 9 to about 15 chosen from alkylpolyglucosides, polyglycerol-based emulsifiers, sorbitan fatty esters, sugar fatty esters, polyol fatty esters, glyceryl fatty esters, ethoxylates thereof, or a mixture thereof;

(f) about 1 to about 10 wt. % of one or more fatty alcohols;

(g) about 5 to about 20 wt. % of one or more fatty compounds; and (h) one or more thickening polymers;

wherein the composition is oil in water emulsion, and all percentages by weight are based on the total weight of the cosmetic composition.

2. The composition of claim 1, wherein the one or more glyceryl esters are chosen from glyceryl behenate, glyceryl erucate, glyceryl hydroxystearate, glyceryl lanolate, glyceryl laurate, glyceryl myristate, glyceryl palmitate lactate, glyceryl stearate, glyceryl dioleate, glyceryl distearate, glyceryl laurate, or a mixture thereof.

3. The composition of claim 1, further comprising:

(i) about 0.1 to about 5 weight wt. % of 4-tert-butylcyclohexanol.

4. The composition of claim 1 comprising one or more ethoxylated fatty acids.

5. The composition of claim 1, wherein the one or more fatty alcohols are chosen from fatty alcohols having from 8 to 24 carbon atoms.

6. The composition of claim 5, wherein the fatty alcohols are chosen from cetyl alcohol, stearyl alcohol, cetearyl alcohol, behenyl alcohol, lauryl alcohol, myristic or myristyl alcohol, arachidyl alcohol, lignoceryl alcohol, or mixtures thereof.

7. The composition of claim 1, wherein the one or more fatty compounds are chosen from fatty esters, polyolefins, waxes, squalane, squalene, hydrogenated polyisobutene, hydrogenated polydecene, polybutene, mineral oil, pentahydrosqualene, plant and/or vegetable oil, hydrocarbon-based oils, and a mixture thereof.

8. The composition of claim 1, wherein the one or more thickening polymers comprise one or more taurate copolymers.

9. The composition of claim 8, wherein the one or more taurate copolymers are chosen from acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof.

10. The composition of claim 1 comprising about 50 to about 85 wt. % of water.

11. The composition of claim 1, further comprising:

(j) one or more water-soluble solvents.

12. The composition of claim 11, wherein the one or more water-soluble solvents are chosen from glycerin, monoalcohols, polyols, glycols, and a mixture thereof.

13. The composition of claim 1, wherein the composition does not visually phase separate of form particulates for at least 2 weeks in storage at 4° C., 25° C., 37° C., and/or 45° C.; and/or the composition does not visually phase separate of form particulates for at least 10 cycles of freeze-thaw testing, wherein the freeze-thaw testing comprises placing the cosmetic composition in a stability chamber and subjecting it to temperature fluctuation at 12-hour intervals, for a first interval of 12 hours at −20° C. followed by a second interval of 12 hours at 25° C.

14. The composition of claim 1 having a pH of about 5 to about 7.

15. The composition of claim 1 having a viscosity of about 20,000 to about 80,000 cPa·s at 25° C., and shear rate of 1 $s^{-1}$ at 25° C.

16. A cosmetic composition comprising:

(a) about 10 to about 40 wt. % of hydroxypropyl tetrahydropyrantriol;

(b) about 30 to about 80 wt. % of water;

(c) about 0.3 to about 5 wt. % of one or more nonionic surfactants chosen from glyceryl esters having an HLB of about 3 to about 10;

(d) about 0.3 to about 5 wt. % of one or more nonionic emulsifiers having an HLB of about 16 to about 18 chosen from ethoxylated fatty acids;

(e) about 0.5 to about 5 wt. % of one or more nonionic emulsifiers having an HLB of about 10 to about 15 chosen from alkylpolyglucosides, polyglycerol-based emulsifiers, sorbitan fatty esters, sugar fatty esters, polyol fatty esters, glyceryl fatty esters, ethoxylates thereof, or a mixture thereof;

(f) about 1 to about 10 wt. % of one or more fatty alcohols having from 8 to 24 carbon atoms;

(g) about 5 to about 20 wt. % of one or more fatty compounds;

(h) one or more taurate polymers chosen from acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, or a mixture thereof; and (i) optionally, about 0.1 to about 5 wt. % of 4-tert-butylcyclohexanol;

wherein the composition is an oil in water emulsion, and all percentages by weight are based on the total weight of the cosmetic composition.

17. A kit comprising the cosmetic composition of claim 1 and one or more additional skin treatment compositions, wherein the cosmetic composition and each of the one or more skin treatment compositions are separately contained.

18. A method for treating skin of a human comprising applying the cosmetic composition of claim 1 to the skin.

* * * * *